(12) United States Patent
Deng et al.

(10) Patent No.: US 8,771,705 B2
(45) Date of Patent: Jul. 8, 2014

(54) COMBINATION OF PROTEIN VACCINE AND MESENCHYMAL STEM CELLS FOR TREATING CANCER

(75) Inventors: Win-Ping Deng, Taipei (TW); Hsiu-Kang Chang, Taipei (TW); Hung-Chien Wei, Taipei (TW); Tsang-Hsien Alexander Wu, Taipei (TW)

(73) Assignees: HealthBanks Biotech Co., Ltd., Taipei (TW); Kooper Biotech Co., Ltd., Taipei (TW)

( * ) Notice: Subject to any disclaimer, the term of this patent is extended or adjusted under 35 U.S.C. 154(b) by 703 days.

(21) Appl. No.: 12/844,044

(22) Filed: Jul. 27, 2010

(65) Prior Publication Data

US 2011/0027311 A1 Feb. 3, 2011

Related U.S. Application Data

(60) Provisional application No. 61/229,726, filed on Jul. 30, 2009.

(51) Int. Cl.
*A61K 39/12* (2006.01)
*A61K 35/12* (2006.01)
*A61K 39/00* (2006.01)

(52) U.S. Cl.
CPC ....... *A61K 39/0011* (2013.01); *A61K 2035/124* (2013.01); *C12N 2710/20022* (2013.01); *A61K 2039/5156* (2013.01); *A61K 2039/545* (2013.01); *A61K 2039/5158* (2013.01); *A61K 2039/6037* (2013.01)
USPC .................................... 424/204.1; 424/277.1

(58) Field of Classification Search
None
See application file for complete search history.

(56) References Cited

U.S. PATENT DOCUMENTS 7,378,100 B2 * 5/2008 Chang et al. ............... 424/204.1

OTHER PUBLICATIONS

Luznik et al. (Blood, 2003, vol. 101, p. 1645-1652).*
Studeny et al. (Journal of the National Cancer Institute, 2004, vol. 96, p. 1593-1603).*
Hung et al. (Clinical Cancer Research, 2005, vol. 21, p. 7749-7756).*
Hung et al. (International Cancer Research, 2004, vol. 110, p. 313-319 in IDS on Jul. 27, 2010).*
Wei et al. (Molecular Therapy, 2011, p. 1-9).*
Shih-Chieh Hung, et al., (2004) "Immortalization Without Neoplastic Transformation of Human Mesenchymal Stem Cells by Transduction with HPV16 E6/E7 Genes" Int. J. Cancer: 110, 313-319.
Hsin-Ell Wang, et al., (2006) "Molecular Imaging with 123I-FIAU, 18F-FUdR, 18F-FET, and 18F-FDG for Monitoring Herpes Simplex Virus Type 1 Thymidine Kinase and Ganciclovir Prodrug Activation Gene Therapy of Cancer" J Nucl Med 47:1161-1171.
Win-Ping Deng, et al., (2006) "Serial In Vivo Imaging of the Lung Metastases Model and Gene Therapy Using HSV1-tk and Ganciclovir" The Journal of Nuclear Medicine vol. 47 • No. 5.
T R.J. Evans et al., "Vaccine therapy for cancer—fact or fiction?" Q J Med 1999, 92: 299-307.

* cited by examiner

*Primary Examiner* — Agnieszka Boesen
(74) *Attorney, Agent, or Firm* — Hsiu-Ming Saunders; Intellectual Property Connections, Inc.

(57) ABSTRACT

A method for inhibiting growth and/or metastasis of a tumor in a mammal is disclosed. The method comprises administering to a mammal in need thereof an effective amount of stem cells comprising a transgene encoding at least one oncogenic protein, wherein the stem cells are immortal and show no signs of neoplastic transformation; and administering to the mammal a vaccine composition comprising an effective amount of at least one immunogenic protein capable of eliciting at least one antibody specific against the at least one oncogenic protein, and thereby inhibiting growth and/or metastasis of a tumor in the mammal. A therapeutic kit for inhibiting growth and/or metastasis of a tumor in a mammal is also disclosed.

9 Claims, 6 Drawing Sheets

COMBINATION OF PROTEIN VACCINE AND MESENCHYMAL STEM CELLS FOR TREATING CANCER

REFERENCE TO RELATED APPLICATION

The present application claims the priority to U.S. Provisional Application Ser. No. 61/229,726, filed Jul. 30, 2009, which is herein incorporated by reference in its entirety.

FIELD OF THE INVENTION

The present invention relates generally to a cancer therapy, and more specifically to an anticancer vaccine therapy.

BACKGROUND OF THE INVENTION

Despite advances in both clinical and basic research dedicated to reducing mortality rates and improving survival, cancer remains the leading cause of death among patients under 85 years of age in the United States. Most deaths from cancer do not result from the primary tumor but rather from the later metastasis. As a result, systemic therapy has become an essential component of metastatic cancer management. Systemic therapy has been limited to chemotherapy and biologic response modifiers. While new therapeutic agents like docetaxel, pernetrexed and erlotinib have been demonstrated as being effective in treating patients with advanced lung cancer, clinical responses to treatment and improved survival have been modest. The limited success of systemic chemotherapy thus underscores the need in developing adjunctive therapies.

Cancer vaccine therapy appears to be an attractive approach for cancer treatment because of its potential in eradicating systemic tumors at multiple sites and specificity in discriminating normal cells from neoplastic cells. Unlike most vaccines for infectious agents, the goal of cancer vaccination is therapeutic and this can be achieved by activating immune responses against tumor antigens. The immune response can be crudely divided into either antibody responses or T-cell responses. Antibodies recognize and bind to conformational determinants on cell surface proteins, and can kill the cell by either antibody-dependent cellular cytotoxicity or complement-mediated cell lysis. Conversely, T cells recognize small peptides presented on the cell surface on major histocompatibility (MHC) antigens, and T-cell activation requires a co-stimulatory signal which is usually present on the cell surface of antigen-presenting cells. However, attempts to exploit the immune system as a therapeutic strategy in cancer treatment have to overcome the host's inability to develop effective endogenous immunity against cancer.

The notion of directing the immune response towards a selected antigen should give potentially greater control of the immune response. However tumor-associated antigens have not been identified for most tumors, and where these have been identified, they may not be the most potent antigens involved in the rejection of that particular tumor, so that vaccine design may be suboptimal.

Therefore, a heretofore unaddressed need exists in the art to address the aforementioned deficiencies and inadequacies, especially in connection with antigen-specific cancer vaccines.

SUMMARY OF THE INVENTION

In one aspect, the invention relates to a method for inhibiting growth and/or metastasis of a tumor in a mammal. The method comprises:

administering to a mammal in need thereof an effective amount of stem cells comprising a transgene encoding at least one oncogenic protein, wherein the stem cells are immortal and show no signs of neoplastic transformation;

administering to the mammal a vaccine composition comprising an effective amount of at least one immunogenic protein capable of eliciting at least one antibody specific against the at least one oncogenic protein;

allowing the at least one immunogenic protein to elicit the at least one antibody specific against the at least one oncogenic protein in the mammal; and allowing the elicited at least one antibody to induce tumor cell death and thereby inhibiting growth and/or metastasis of the tumor in the mammal.

In another aspect, the invention relates to a method for inhibiting growth and/or metastasis of a tumor in a mammal, which comprises:

administering to a mammal in need thereof an effective amount of stem cells comprising a transgene encoding at least one HPV Envelope protein selected from the group consisting of E7, E6 and a combination thereof, wherein the stem cells are immortal and show no signs of neoplastic transformation;

administering to the mammal a vaccine composition comprising at least one immunogenic protein capable of eliciting at least one antibody specific against the at least one HPV protein selected from the group consisting of E7, E6 and a combination thereof;

allowing the at least one immunogenic protein to elicit the at least one antibody specific against the at least one HPV protein in the mammal; and allowing the elicited at least one antibody to induce tumor cell death and thereby inhibiting growth and/or metastasis of the tumor in the mammal.

Further in another aspect, the invention relates to a therapeutic kit for inhibiting growth and/or metastasis of a tumor in a mammal. The kit comprises: a) stem cells comprising a transgene encoding at least one HPV protein selected from the group consisting of E7, E6 and a combination thereof, wherein the stem cells are immortal and show no sign of neoplastic transformation; b) a vaccine composition comprising at least one immunogenic protein capable of eliciting at least one antibody specific against the at least one HPV protein selected from the group consisting of E7, E6 and a combination thereof; and c) a package insert containing printed instructions for performing a method for inhibiting growth and/or metastasis of a tumor in a mammal as aforementioned.

Yet in another aspect, the invention relates to a therapeutic kit for inhibiting growth and/or metastasis of a tumor in a mammal, which comprises: a) stem cells comprising a transgene encoding at least one oncogenic protein, wherein the stem cells are immortal and show no sign of neoplastic transformation; b) a vaccine composition comprising an effective amount of at least one immunogenic protein capable of eliciting at least one antibody specific against the at least one oncogenic protein; and c) a package insert containing printed instructions for performing a method for inhibiting growth and/or metastasis of a tumor in a mammal as aforementioned.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention.

Wherever possible, the same reference numbers are used throughout the drawings to refer to the same or like elements of an embodiment.

DETAILED DESCRIPTION OF THE INVENTION

Definitions

Figure 1A:
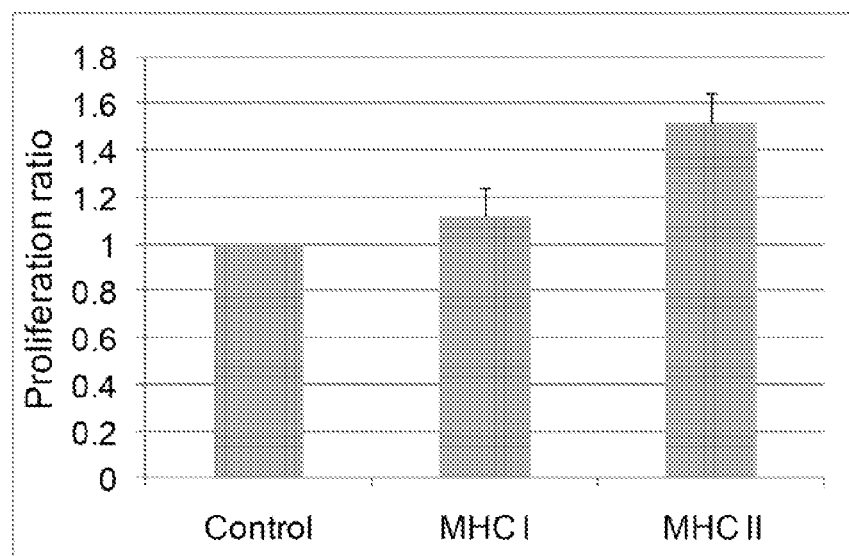
FIG. 1A is a graph showing that E7 peptide containing MHC class II epitope stimulated the proliferation of splenocytes isolated from mice vaccinated with the E7-fusion protein vaccine, PE(ΔIII)-E7-KDEL3.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around," "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "sarcoma" means a malignant tumor arising from connective tissues.

The term "epitope" refers to the minimal structural unit of an antigen, recognizable for antibodies and lymphocyte antigenic receptors.

The term "inhibiting growth and/or metastasis" shall generally mean inhibiting growth or metastasis or both.

In one aspect, the invention relates to a method for inhibiting growth and/or metastasis of a tumor in a mammal. The method comprises:

administering to a mammal in need thereof an effective amount of stem cells comprising a transgene encoding at least one oncogenic protein, wherein the stem cells are immortal and show no signs of neoplastic transformation;

administering to the mammal a vaccine composition comprising an effective amount of at least one immunogenic protein capable of eliciting at least one antibody specific against the at least one oncogenic protein;

allowing the at least one immunogenic protein to elicit the at least one antibody specific against the at least one oncogenic protein in the mammal; and allowing the elicited at least one antibody to induce tumor cell death and thereby inhibiting growth and/or metastasis of the tumor in the mammal.

In one embodiment of the invention, the least one oncogenic protein is selected from the group consisting of HPV E7, HPV E6 and a combination thereof.

In one embodiment of the invention, the transgene encodes at least one oncogenic protein selected from the group consisting of HPV E7, HPV E6 and a combination thereof; and wherein the vaccine composition comprises at least one immunogenic protein capable of eliciting at least one antibody specific against the at least one oncogenic protein selected from the group consisting of HPV E7, HPV E6 and a combination thereof.

In another embodiment of the invention, the method further comprises allowing the transgene of the stem cells to incorporate into cells of the tumor in the mammal.

In another embodiment of the invention, the at least one immunogenic protein comprises at least one Major Histocompatibility Complex (MHC) class II epitope.

In another embodiment of the invention, the method further comprises allowing the at least one immunogenic protein to stimulate proliferation of CD4+ T-cells.

In another embodiment of the invention, the method further comprises allowing the elicited at least one antibody to trigger complement-dependent tumor cell lysis.

In another embodiment of the invention, the stem cells and the vaccine composition are sequentially administered to the mammal.

In another embodiment of the invention, the stem cells and the vaccine composition are concurrently administered to the mammal.

In another embodiment of the invention, the stem cells are mesenchymal stem cells.

In another embodiment of the invention, the mesenchymal stem cells are derived from bone marrow or cord blood.

In another embodiment of the invention, the tumor is at least one selected from the group consisting of a lung tumor and a sarcoma.

In another embodiment of the invention, the mammal has metastatic cancer.

In another embodiment of the invention, the stem cells comprises a transgene encoding a human papillomavirus (HPV) Envelope protein selected from the group consisting of HPV E7, HPV E6, and a combination thereof.

In another embodiment of the invention, the vaccine composition comprises at least one immunogenic protein capable of eliciting at least one antibody specific against the human HPV Envelope protein selected from the group consisting of HPV E7, HPV E6, and a combination thereof.

In another embodiment of the invention, the immunogenic protein comprises a fusion protein comprising: a) a *Pseudomonas* exotoxin A (PE) fragment comprising a binding domain and a translocation domain and without a cytotoxic domain; b) a human papillomavirus (HPV) Envelope protein selected from the group consisting of HPV E7, HPV E 6, and a combination thereof; and c) a carboxyl terminal moiety comprising an endoplasmic retention sequence.

In another embodiment of the invention, the immunogenic protein comprises a fusion protein comprising: a) a *Pseudomonas* exotoxin A (PE) fragment comprising a binding domain and a translocation domain and without a cytotoxic domain; b) a human papillomavirus (HPV) E7 protein; and c) a carboxyl terminal moiety comprising an endoplasmic retention sequence.

In another aspect, the invention relates to a method for inhibiting growth and/or metastasis of a tumor in a mammal, which comprises:

administering to a mammal in need thereof an effective amount of stem cells comprising a transgene encoding at least one HPV Envelope protein selected from the group consisting of E7, E6 and a combination thereof, wherein the stem cells are immortal and show no signs of neoplastic transformation;

administering to the mammal a vaccine composition comprising at least one immunogenic protein capable of eliciting at least one antibody specific against the at least one HPV protein selected from the group consisting of E7, E6 and a combination thereof;

allowing the at least one immunogenic protein to elicit the at least one antibody specific against the at least one HPV protein in the mammal; and allowing the elicited at least one antibody to induce tumor cell death and thereby inhibiting growth and/or metastasis of the tumor in the mammal.

Further in another aspect, the invention relates to a therapeutic kit for inhibiting growth and/or metastasis of a tumor in a mammal. The kit comprises: a) stem cells comprising a transgene encoding at least one HPV protein selected from the group, consisting of E7, E6 and a combination thereof, wherein the stem cells are immortal and show no sign of neoplastic transformation; b) a vaccine composition comprising at least one immunogenic protein capable of eliciting at least one antibody specific against the at least one HPV protein selected from the group consisting of E7, E6 and a combination thereof; and c) a package insert containing printed instructions for performing a method for inhibiting growth and/or metastasis of a tumor in a mammal as aforementioned.

Yet in another aspect, the invention relates to a therapeutic kit for inhibiting growth and/or metastasis of a tumor in a mammal, which comprises: a) stem cells comprising a transgene encoding at least one oncogenic protein, wherein the stem cells are immortal and show no sign of neoplastic transformation; b) a vaccine composition comprising an effective amount of at least one immunogenic protein capable of eliciting at least one antibody specific against the at least one oncogenic protein; and c) a package insert containing printed instructions for performing a method for inhibiting growth and/or metastasis of a tumor in a mammal as aforementioned.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Animals. Four-to-six week-old female FVB/N mice were purchased from the National Taiwan University (Taipei, Taiwan). The animal experiment protocol was approved by the Institutional Animal Care and Use Committee of Taipei Medical University.

Cell lines. Tumor cell line. NG4TL4-STK murine sarcoma cells, which were lung-colonizing metastatic sarcoma cells carrying HSV1-tk gene and were established as disclosed previously, were cultured in minimum essential medium supplemented with 10% fetal bovine, serum, 100 units/mL penicillin, 10 μg/mL streptomycin, and 2 mmol/L L-glutamine in a humidified atmosphere with 5% $CO_2$ at 37° C.

Stem cell line. An actively proliferating human mesenchymal stem cell line called KP-hMSC, which expressed HPV16 E6/E7 mRNA, was originally derived from the bone marrow of a 61-year-old female donor and immortalized by retroviral-mediated transduction of human papilloma virus E6/E7 genes as described previously. See Hung et al., (2004) "Immortalization without neoplastic transformation of human mesenchymal stem cells by transduction with hpv16 e6/e7 genes" *Int. J. Cancer:* 110, 313-319, which is herein incorporated by reference in its entirety. The cell line was maintained in DMEM containing 1 mg/mL glucose and 10% fetal bovine serum, 100 units/mL penicillin, 10 μg/mL streptomycin, and 2 mmol/L L-glutamine in a humidified atmosphere with 5% $CO_2$ at 37° C. This immortalized KP-hMSC cell line was >99% positive for the characteristic markers CD29, CD44, CD90, CD105, SH2, and SH3 MSC.

Animal immunization with E7-fusion protein vaccine. A vaccine composition comprising the E7-fusion protein PE(ΔIII)-E7-KDEL3 was disclosed in the U.S. Pat. No. 7,378,100 and kindly provided by Dr. C. W. Liao at Animal Technology Institute Taiwan, Miaoli, Taiwan. The fusion protein PE(ΔIII)-E7-KDEL3 comprises a first polypeptide fragment from *Pseudomonas aeruginosa*, a second polypeptide from HPV16 E7 protein (SEQ ID NO: 1; NCBI Reference Sequence: NP_041326.1), and a carboxyl terminal moiety which comprises an endoplasmic reticulum (ER) retention sequence KDEL (SEQ ID NO: 2). The first polypeptide fragment PE(ΔIII) comprises a binding domain (domain I) and a translocation domain (domain II) but is devoid of a cytotoxic domain (domain III). The carboxyl terminal moiety comprises an ER retention sequence KDEL. The first polypeptide fragment PE(ΔIII) and carboxyl terminal moiety having an ER retention sequence KDEL are disclosed in U.S. Pat. Nos. 7,378,100; 7,335,361, 7,465,455 and U.S. Publication Number 20080206271, all of which are herein incorporated by reference in their entireties.

The stock of PE(ΔIII)-E7-KDEL3 was diluted with PBS and incubated for 2 hours at 37° C. before vaccination. Mice were immunized with 0.1 mg/mouse PE(ΔIII)-E7-KDEL3 mixed with 10% ISA206™ adjuvant by subcutaneously injection into the back of the mice. The mice were boosted twice subcutaneously 1 and 2 weeks later using the same regimen.

Splenocyte proliferation assay. Splenocytes were harvested from mice 1 week after the last vaccination. Proliferation of splenocytes was determined in vitro using 5-bromo deoxyuridine (BrdU) cell proliferation assay kit (CHEMICON) according to the manufacturer's instructions. Before the cell proliferation assay, $1 \times 10^5$ pooled splenocytes from immunized or naïve mice were incubated for 6 days with either 1 μg/ml of E7 peptide (residues 49-57; SEQ ID NO: 3) containing an MHC class I epitope for detecting E7-specific $CD8^+$-T cell precursors or 1 μg/ml of E7 peptide (residues 30-67; SEQ ID NO: 4) containing an MHC class II epitope for detecting E7-specific $CD4^+$-T cell precursors.

Dot blot assay. E7 protein was blotted onto nitrocellulose membrane (Bio-Rad). The membrane was blocked with a blocking buffer (5% skim milk in TBST) for 1 hr and then blocking solution was discarded. The membrane was incubated with serial diluted serum at 4° C. overnight. Antibody binding was detected by incubation of the membrane with goat anti-mouse IgG-horse radish peroxidase (HRP), which was followed by Western Lighting™ Chemiluminescence Reagent Plus assay (PerkinElmer) according to the manufacturer's protocol.

Cytotoxicity assay. NG4TL4-STK and KP-hMSC cells/well (1:1, $1 \times 10^4$ in total) were seeded in 96-well plates overnight and followed by the addition of serum from vaccinated mice for 3 days. Cytotoxicity assay was performed by quantitative measurements of lactate dehydrogenase (LDH) using CYTOTOX-ONE™ Homogeneous Membrane Integrity Assay (PROMEGA™) according to the vendor's protocol.

Figure 2A:
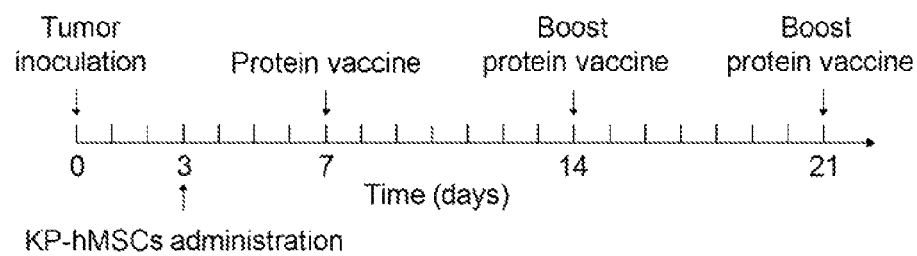
FIG. 2A shows a dosing schedule of a combination treatment with E7-fusion protein vaccine and KP-hMSCs in a tumor-bearing mouse model.

Tumor-bearing mouse models and experimental groups. Two mouse tumor models were established. One was a subcutaneous tumor model and the other was an intravenous or lung metastasis model. Briefly, tumor xenografts were established by subcutaneous injection of $5 \times 10^4$ or intravenous injection of $1 \times 10^5$ NG4TL4-STK cells on day 0. In each mouse tumor model, there were four experimental groups: The tumor-bearing mice in the untreated control group received PBS; mice in the vaccine-only treated group received the E7 fusion protein vaccine alone (i.e., PE(ΔIII)-E7-KDEL3); mice in the MSCs-only-treated group received KP-hMSCs alone; and mice in the combination treatment group received both the E7 fusion protein vaccine and KP-hMSCs (KP-hMSC+PE(ΔIII)-E7-KDEL3). To administer stem cells, mice were injected intravenously KP-hMSCs on day 3 (FIG. 2A). To vaccinate animals, mice were immunized with PE(ΔIII)-E7-KDEL3 protein vaccine 7 days after the tumor inoculation and received boost shots 1 and 2 weeks later (FIG. 2A).

Molecular imaging for monitoring tumor responses during cancer therapy. Planar γ-imaging was obtained on day 6, 20 and 34 after inoculation of NG4TL4-STK cells in the subcutaneous tumor model. In the lung-metastasis model, planar γ-imaging was obtained on 7 and 14 days post-inoculation (i.v. NG4TL4-STK cells). Planar γ-imaging was performed as described (Deng et al., (2006) "Serial In Vivo Imaging of the Lung Metastases Model and Gene Therapy Using HSV1-tk and Ganciclovir"*J. Nucl. Med.* 47:877-884). Briefly, 3.7 MBq of $^{131}$I-FIAU were injected into the tail vein 24 h before planar imaging. Images were collected with a digital γ-camera (Elscint SP-6) equipped with a high-energy pinhole collimator, a 364-keV±10% $^{131}$I photopeak energy window and a 256×256×16 bit image matrix.

Histochemistry. Mice were sacrificed and lung tissues were collected 21 days after tumor inoculation. Lung tissues were fixed in 4% paraformaldehyde and pulmonary tumor nodules in each mouse were evaluated and enumerated by experimenters blinded to the sample identity. For histological analysis, the fixed lung tissues were embedded in paraffin and followed by cutting in 10 μm sections and stained with hematoxylin and eosin (H&E).

Reverse transcription polymerase chain reaction. Total RNA harvested from NG4TL4-STK cells and tumors was extracted using TRIzol reagent (Invitrogen Life Technologies) and underwent reverse transcription (RT) followed by PCR amplification. Reverse transcription was performed with SUPERSCRIPT™ III (Invitrogen Life Technologies) and an Oligo $(dT)_{12-18}$ primer. Four micrograms of RNA were added into a final volume of 21-μL solution containing 10 mM deoxynucleotide triphosphate mix, 10×RT buffer, 25 mM $MgCl_2$, 0.1 M dithiothreitol, RNase inhibitor and RNase H. Six micrograms of RT product were used for PCR amplification in a final volume of 50 μL containing 2.5 mM deoxynucleotide triphosphate, 25 mM $MgCl_2$, primers, and Taq DNA polymerase (Invitrogen Life Technologies). PCR amplification of reverse-transcribed cDNA was performed with the following primers and conditions. The primers used for HSV1-tk were 5' TGCAGCGACCCGCTTAACAGCGT 3' (forward; SEQ ID NO: 5) and 5' CATAGATCTGGATC-CTTCCGGTATTGTCT 3' (reverse; SEQ ID NO: 6). Tm: 55° C., 35 cycles. The primers for HPV16 E6/E7 were 5' ATG-CATAGTATATAGAGATGGGAAT 3' (forward; SEQ ID NO: 7) and 5' CTGCAGCATCAGCCATGGTAGA 3' (reverse; SEQ ID NO: 8). Tm: 56° C., 35 cycles. The primers for GAPDH were 5' GCTCTCCAGAACATCATCCCTGCC 3' (forward; SEQ ID NO: 9) and 5' CGTTGTCATACCAG-GAAATGAGCTT 3' (reverse; SEQ ID NO: 10). Tm: 55° C., 35 cycles. PCR products were run on 1% agarose gels (AM-RESCO) and visualized with ethidium bromide staining. Images were analyzed using FloGel-1 (Fluorescent Gel Image System; TOP BIO Co.). GAPDH was used as an internal control.

Western Blot Analysis. Recombinant E7 protein was loaded onto a SDS-polyacrylamide gel and separated by electrophoresis. For Western blotting, proteins from gels were transferred to a PVDF membrane (pore size, 0.5 µm; Schleicher and Schuellx) using a Mini Trans-Blot Cell apparatus (Bio-Rad Laboratories). The PVDF membrane was probed with a 1:6,000 diluted serum from mice with combination treatment group or KP-hMSCs-only treated group. The E7-specific antibody was detected by incubation with goat anti-mouse IgG-HRP and followed by Western Lighting™ Chemiluminescence Reagent Plus assay (PerkinElmer) according to the manufacturer's protocol.

TUNEL assay. TUNEL assay was performed using DeadEnd colorimetric apoptosis detection system (Promega) according to the manufacturer's instructions. Briefly, subcutaneous tumor sections from mice of combined-treatment group or KP-hMSCs-only treated group were made permeable with 20 µg/ml proteinase K for 10 min at room temperature and the fragmented DNA was labeled using terminal deoxynucleotidyl transferase (TdT) reaction mixture containing green fluorescein-12-dUTP for 1 h at 37° C. according to supplier's recommendations. Nuclei were stained with 1 µg/ml propidium iodide (PI). The result of TUNEL assay was expressed quantitatively using the ratio of apoptotic cells/field of view.

Example 1

E7 as a Dominant MHC Class II Antigen

To investigate the immunological response stimulated by the E7-fusion protein vaccine PE(ΔIII)-E7-KDEL3, splenocytes isolated from the vaccinated and naïve mice were incubated with an E7 peptide fragment containing MHC class I epitope (the amino acids 49-57; SEQ ID NO: 3) and an E7 peptide fragment containing MHC class II epitope (the amino acids 30-67; SEQ ID NO: 4), respectively. FIG. 1A shows the results of splenocyte proliferation assay in response to E7 peptide immunogen in vitro. Splenocytes from the mice vaccinated with PE(ΔIII)-E7-KDEL3 showed an increased proliferation in response to the E7 peptide containing MHC class II-epitope. After a 5-day incubation period, splenocytes cultured with the E7 peptide fragment containing MHC class II epitope exhibited a significantly increased proliferation rate, indicating that the fusion protein PE(ΔIII)-E7-KDEL3 could stimulate proliferation of E7-specific CD4+ T-cell precursors but not CD8+ T-cell precursors.

Example 2

E7 Antibody-Dependent Cytotoxicity

Figure 1B:
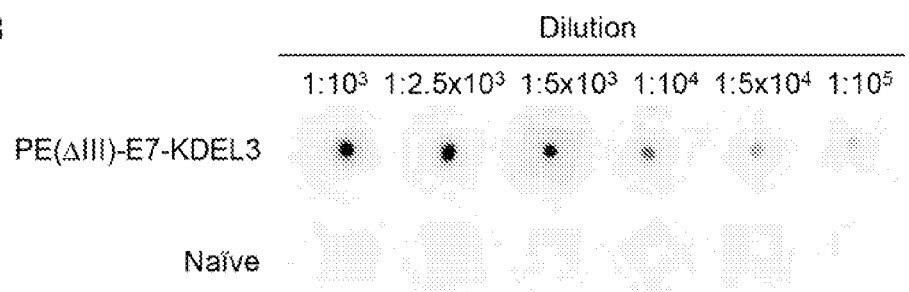
FIG. 1B is a photograph showing the result of a Dot blot analysis of serum from E7-fusion protein-vaccinated and naïve mice.

Dot blot analysis was used to demonstrate the relative E7-specific antibody titer elicited by the E7-fusion protein vaccine. The results of Dot blot analysis indicated that serum from a mouse vaccinated with PE(ΔIII)-E7-KDEL3 contained E7-specific antibody, as shown in FIG. 1B.

Figure 1C:
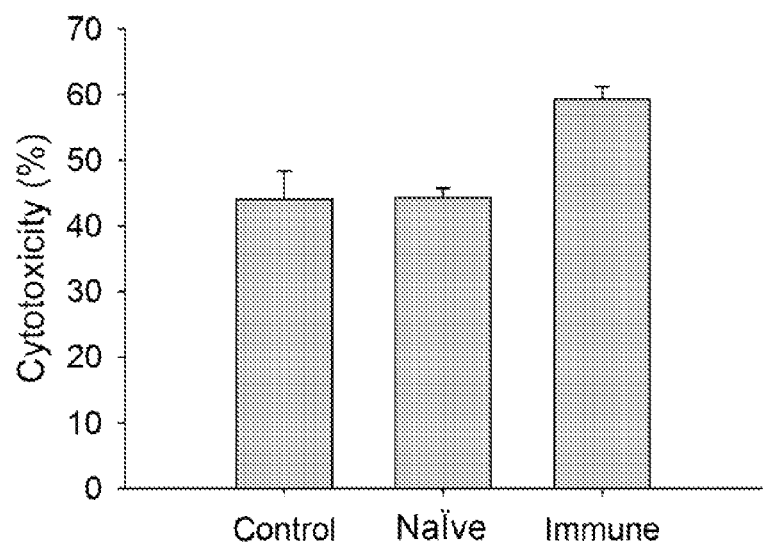
FIG. 1C is a graph showing the cytotoxic effect of sera from E7-fusion protein vaccine-immunized mice on cell co-culture of NG4TL4-STK and KP-hMSCs.

Antibody-mediated tumor immunity can be achieved by complement dependent cytotoxicity (CDC) and antibody dependent cell-mediated cytotoxicity (ADCC). A cytotoxicity assay demonstrated that anti-E7 serum increased the incidence of cell lysis in NG4TL4-STK/KP-hMSCs co-culture. After incubation with the co-culture of NG4TL4-STK and KP-hMSC cells, sera from mice vaccinated with PE(ΔIII)-E7-KDEL3 induced more cell lysis than sera from naïve mice, as shown in FIG. 1C. The results indicated that E7-specific antibody mediated complement-dependent cytotoxicity.

Example 3

Tumor Inhibitory Response to the Combination Therapy

Planar γ-imaging was performed for monitoring tumor responses to the combined treatment with E7-fusion protein vaccine and MSCs in an experimental cancer mouse model. The time course of the experiment design is illustrated in FIG. 2A. Briefly, mice were inoculated with NG4TL4-STK sarcoma cells on day 0 followed by intravenous injection of KP-hMSCs (stem cell line derived from human bone marrow) on day 3. Mice were immunized with the E7 fusion protein vaccine PE(ΔIII)-E7-KDEL3 seven days after the tumor inoculation and received boost shots 1 and 2 weeks thereafter.

Figure 2B:
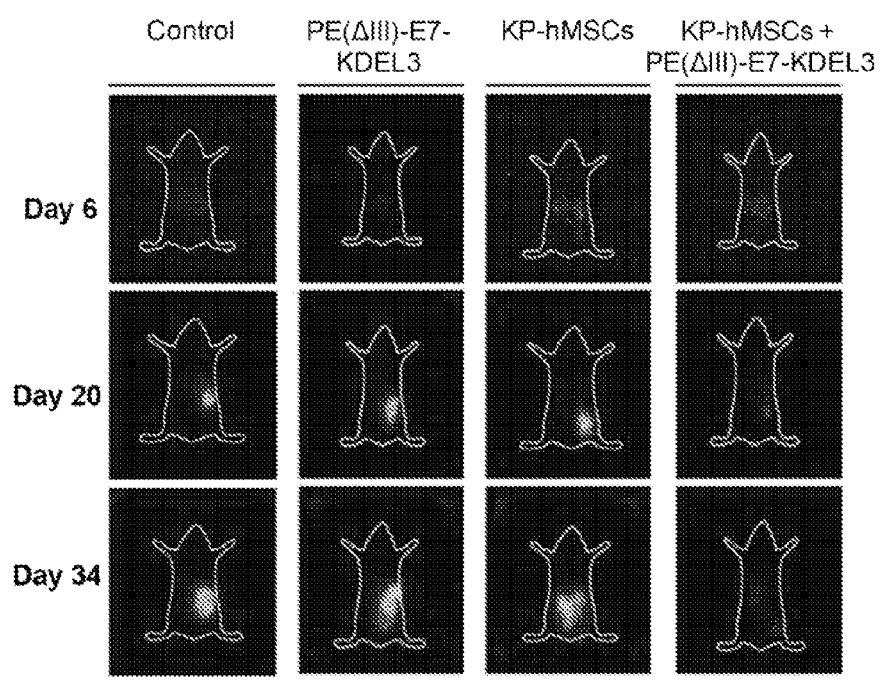
FIG. 2B shows planar γ-images of subcutaneous tumor xenografts in mice of different treatment groups.

In the subcutaneous tumor model, planar γ-imaging was performed after the s.c. inoculation of NG4TL4-STK cells. FIG. 2B shows representative planar γ-camera images from the subcutaneous tumor model. Images were taken 6, 20 and 34 days after s.c injection of $5 \times 10^4$ NG4TL4-STK cells in the right flanks. The signal intensity reflected the extent and relative growth of tumor. The images from the combination treatment group showed a significant lower level of signal intensity on day-20 and 34, reflecting a reduced tumor burden over time, while a reversed result was observed in the control animals.

Figure 2C:
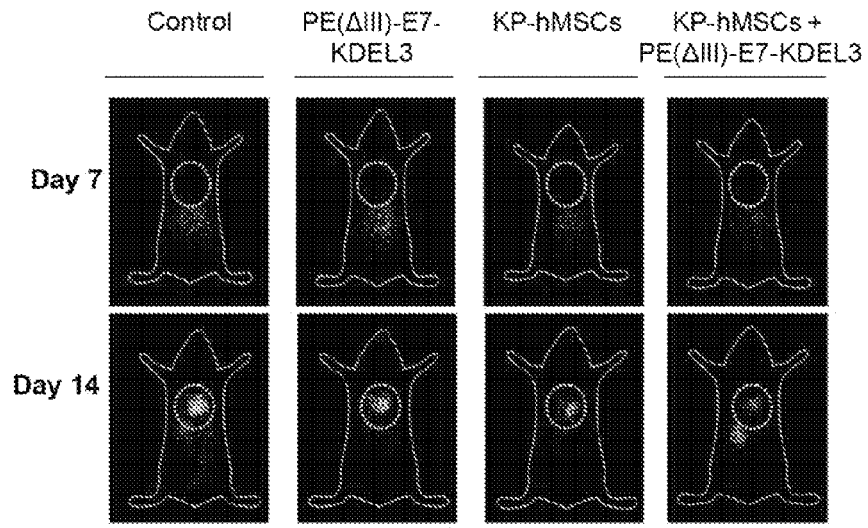
FIG. 2C shows planar γ-images of intravenous tumor xenografts in mice of different treatment groups.

In the lung metastasis model, mice had received intravenous inoculation of NG4TL4-STK sarcoma cells and were subjected to planar γ-imaging post-inoculation. FIG. 2C shows representative planar γ-camera images of the lung metastasis model. Images were collected on 7 and 14 days post i.v. injection of $1 \times 10^5$ NG4TL4-STK cells. No signals were detected in the lung on day 7 in all the groups. On day 14, signals from the tumors containing NG4TL4-STK sarcoma cells were detected in the lungs of all the groups, an indication of lung metastasis. Among the four experimental groups, mice having received the combined treatment exhibited the weakest tumor signal intensity, which was similar to the finding in the subcutaneous model. Dotted circle represents the position of the lung tissue.

The results from both subcutaneous and lung-metastasis animal models suggested that a combination therapy produced an inhibitory effect on tumor growth and lung metastasis.

Example 4

Histochemical Validations of Whole Body Imaging Data

Figure 3A:
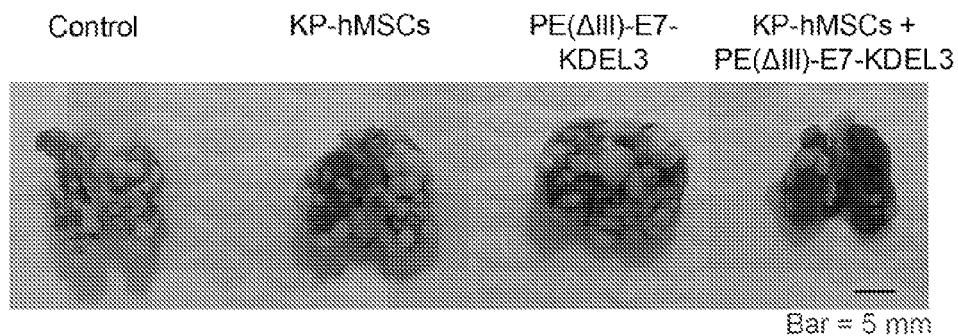
FIG. 3A shows photographs of pulmonary nodules in the lung tissues from mice of different treatment groups.

To validate the in vivo imaging experiments, lung tissues of mice receiving tumor grafts via an intravenous route were collected 21 days after tumor inoculation. The macromorphological analysis showed that there were fewer pulmonary nodules in the combined treatment group than in other groups. FIG. 3A shows representative macro-morphological images of pulmonary nodules from different treatment groups. The lung tissue from the combined treatment group had the least number of tumor nodules.

Figure 3B:
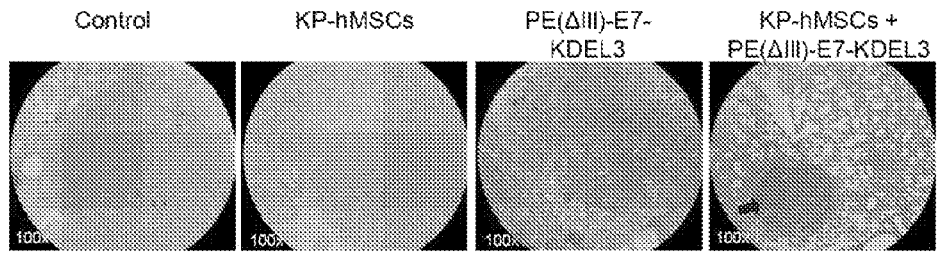
FIG. 3B shows photomicrographs of sections of lung tissues of FIG. 3A.

The lung tissues from combined treatment group also demonstrated a higher degree of structural integrity as evidenced by the presence of intact pulmonary alveoli (hollow cavities in FIG. 3B). FIG. 3B shows H&E stained paraffin sections of lung tissues from different treatment groups. Pulmonary alveoli appeared more intact in the combined treatment group than other groups. The arrow indicated tumor nodule formation.

Figure 3C:
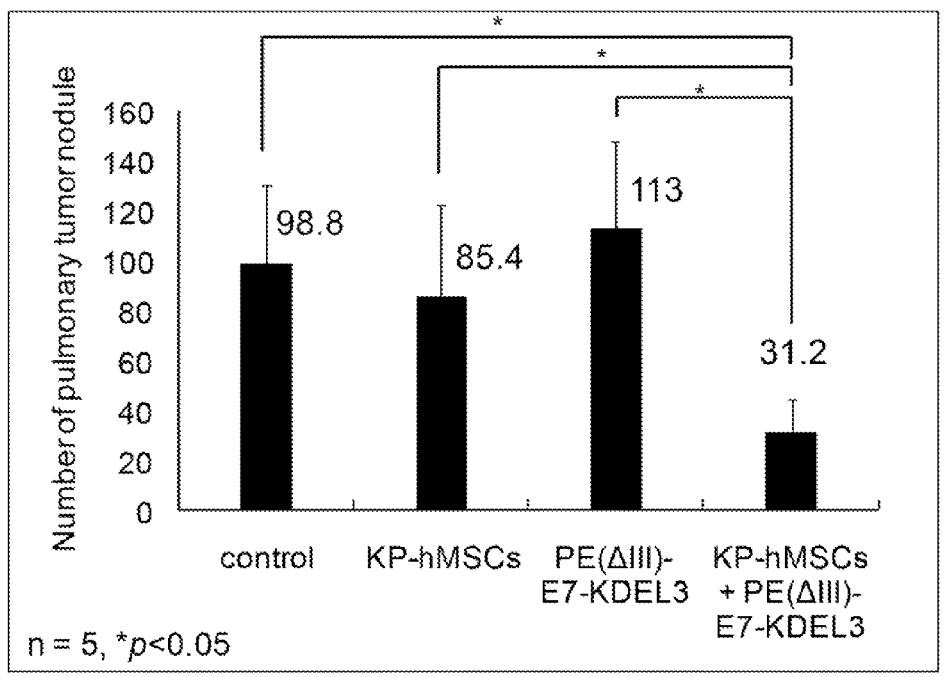
FIG. 3C is a graph showing the numbers of tumor nodules in the lung tissues of FIG. 3A.

FIG. 3C shows quantification of pulmonary nodules from control and treatment groups. A significant decrease in the number of pulmonary nodules was observed in the combined treatment group as compared with other groups. *P<0.05 using paired t-test.

Example 5

Homing of MSCs to Cancer Cells

Figure 4A:
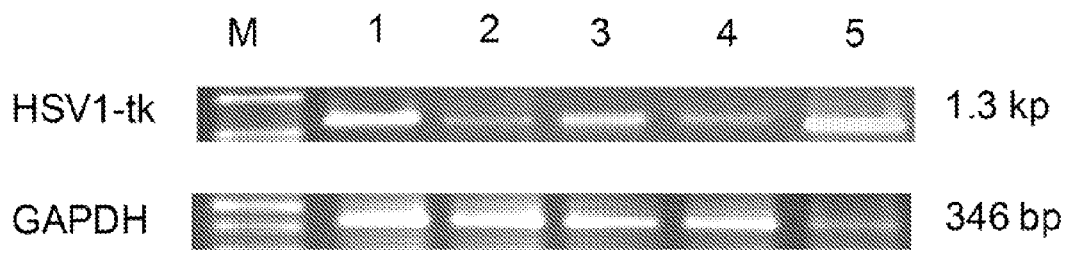
FIG. 4A is a photograph of gel electrophoresis showing the results of RT-PCR analysis of HSV1-tk gene expression products in the lung tissues from intravenously xenografted mice of different treatment groups.

To confirm that the lung metastatic tumors were indeed developed from herpes simplex virus type 1 thymidine kinase (HSV1-tk)-transduced NG4TL4-STK sarcoma cells, HSV1-tk gene expression level in the tumor tissues was measured using semi-quantitative RT-PCR. The HSV1-tk gene was used as an indicator that the pulmonary tumors were developed from NG4TL4-STK cells and thus could be detected in all animal groups. FIG. 4A shows PCR detection of HSV1-tk gene expression products in all groups. The mRNA level of HSV1-tk appeared to be lower in the samples from the vaccine-only treated (lane 2) and combined treatment groups (lane 4). Lane 1: sample from the untreated control group; lane 2: sample from the vaccine-only treated group; lane 3: sample from the KP-hMSCs-only treated group; lane 4: sample from the combined treatment group; lane 5: NG4TL4-STK cells (positive control).

Figure 4B:
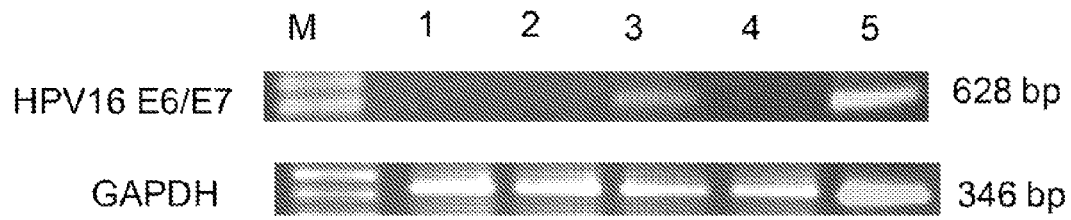
FIG. 4B is a photograph of gel electrophoresis showing the results of RT-PCR analysis of HPV16 E6/E7 gene expression products in the lung tissues from mice of different treatment groups.

In a parallel experiment, the HPV 16 E6/E7 transgene expression levels in the lung tissues from mice of different treatment groups were detected by RT-PCR to identify KP-hMSCs. As shown in FIG. 4B, HPV 16 E6/E7 mRNA was detected in the lung tissue of mice treated with KP-hMSCs only (lane 3), verifying that MSCs could target and infiltrate tumors. However, HPV 16 E6/E7 mRNA was not detected in the sample from the combined treatment group (lane 4). Lane 1: sample from the untreated control; lane 2: sample from the PE(ΔIII)-E7-KDEL3 fusion protein vaccine-treated group; lane 3: sample from the KP-hMSCs-treated group; lane 4: sample from the combined treatment group; lane 5: KP-hMSCs (positive control). GAPDH was used as an internal standard. The term "M" represents a standard DNA ladder.

Example 6

Combination Treatment with E7-Fusion Protein Vaccine and E6/E7-Engineered MSCs Correlated with Anti-Tumor Effect The E7-fusion protein vaccine PE(ΔIII)-E7-KDEL3-induced immunity was predominantly mediated by antibody-dependent mechanisms as shown in FIG. 1. To validate this notion, the relationship between serum concentration of anti-E7 antibody and tumor volume was analyzed.

Figure 5A:
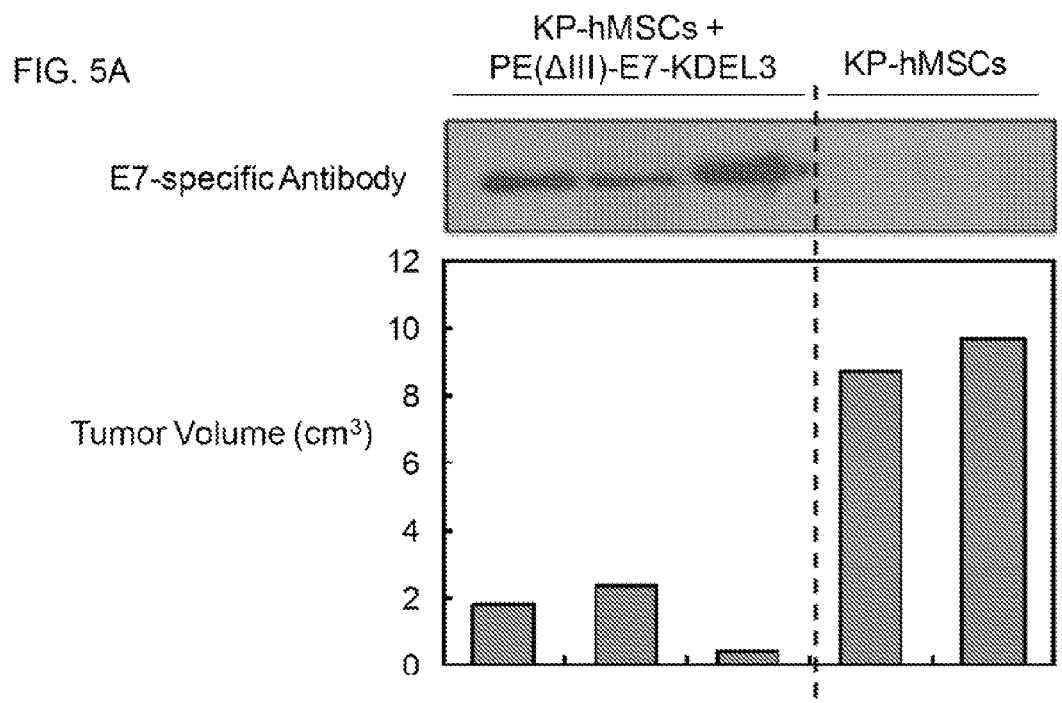
FIG. 5A is a photograph of Western blot analysis of sera from subcutaneously xenografted mice of KP-hMSCs-plus-E7-fusion protein vaccine-treated (i.e., co-treated, top panel, left) and KP-hMSCs-treated groups (top panel, right). The lower panel is a chart showing the size of tumor for the animals in the panel above.

In FIG. 5A, the top panel shows Western blots probed with sera from subcutaneously xenografted mice receiving the combined treatment (top panel, left), and from mice treated with KP-hMSCs only (top panel, right). The sera from mice of combination treatment contained anti-E7 antibody. The lower panel shows the size of the subcutaneous tumor in each mouse, indicating a negative correlation between the titer of anti-E7 antibody and tumor volume. In the combined treatment group (KP-hMSC+PE(ΔIII)-E7-KDEL3), three animals showed a substantially smaller tumor burden than those treated with only the stem cells KP-hMSCs (lower panel). The tumor growth inhibition was correlated with the significantly higher serum concentration of anti-E7 antibody (top panel).

Figure 5B:
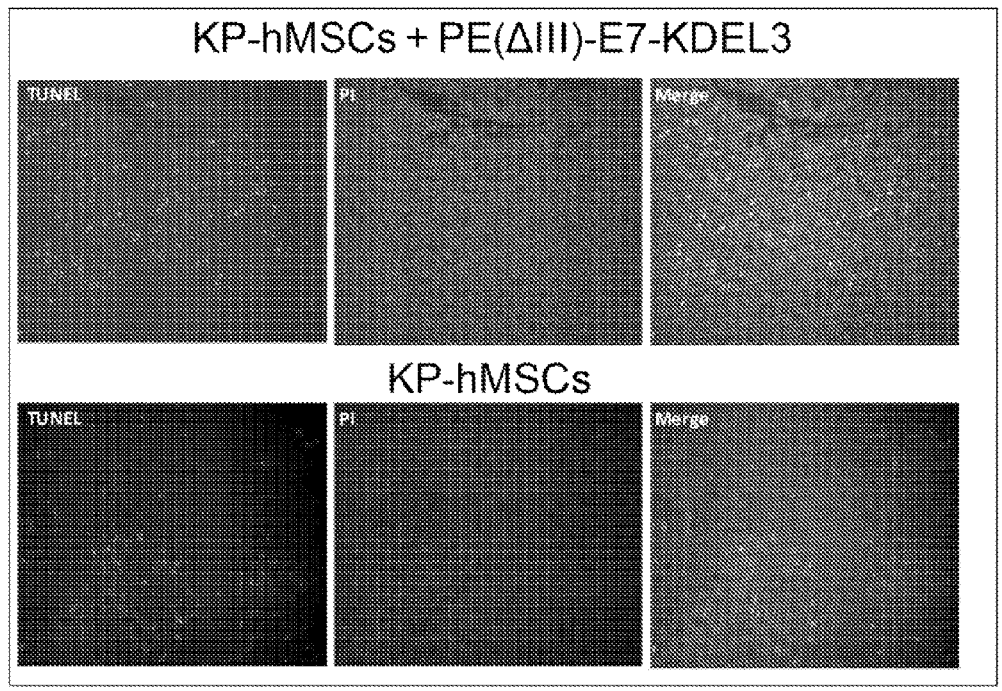
FIG. 5B shows fluorescent photomicrographs of TUNEL staining of subcutaneous tumor sections from mice of KP-hMSCs-plus-E7-fusion protein vaccine-co-treated (top panel) and the stem cells KP-hMSCs-only-treated (lower panel) groups. The middle panel is propidium iodide staining of the same sections. The right panel is an overlay of the paired images. Magnification: 100×.

To examine whether the combined treatment could induce tumor apoptosis, TUNEL assay was performed. FIG. 5B shows a TUNEL analysis of tumor sections obtained from combined treatment and KP-hMSCs-only treatment groups. A TUNEL staining gives green and a propidium iodide staining gives red fluorescence. The data shows that samples from the combined treatment group had more TUNEL-positive cells than those from KP-hMSCs-only treatment group.

Figure 5C:
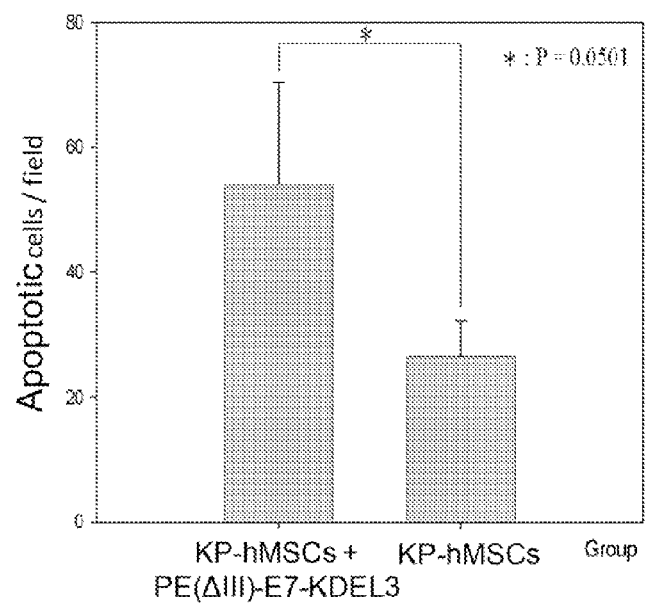
FIG. 5C is a graph showing the number of apoptotic cells per view field in the subcutaneous tumor sections of FIG. 5B.

FIG. 5C shows the quantification of TUNEL analysis, *P=0.0501 using paired t-test. The group treated with KP-hMSC+PE(ΔIII)-E7-KDEL3 demonstrated a significantly higher number of apoptotic cells when compared to the group treated with the stem cells KP-hMSCs only. As shown in FIG. 5C, the number of apoptotic cells per field of view in the tumor sections from the mice treated with KP-hMSC+PE(ΔIII)-E7-KDEL3 was higher than that from the mice treated with KP-hMSCs only. Quantitatively, an approximately 2-fold increase in apoptotic cells was observed in the tumor sections from the combination treatment group when compared with the sections from the KP-hMSC-only treatment group.

Example 7

Cord Blood-Derived Mesenchymal Stem Cells Merge with Tumor Cell

Figure 6A:
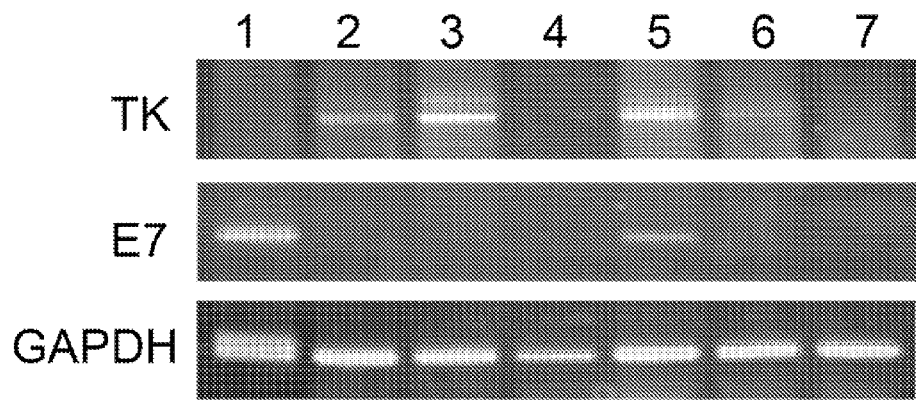
FIG. 6A is a photograph of gel electrophoresis showing the results of RT-PCR analysis of HSV1-tk and E7 gene expression products in the clones obtained from cell co-culture of E7-transduced cord blood-MSCs and NG4TL4-STK cell. Lane 1: E7-transduced cord blood-MSCs (positive control); lanes 2, 3 and 6: clones containing only tk gene; lane 5: fusion clone containing both tk and E7 genes.

To demonstrate that the characteristics of infiltration and incorporation of E7-expressing MSCs into target tumor cells were not limited to the KP-MSC cell line, MSCs isolated from cord blood (CB-MSCs) were co-cultured with NG4TL4-STK tumor cells. CB-MSCs were first transduced with non-functional E7 antigen-encoding gene and puromycin-resistant gene while HSV1-tk-transduced NG4TL4-STK sarcoma cells were transduced with neomycin-resistant gene. The results showed that co-culturing gave rise to hybrid cells that are resistant to both puromycin and neomycin. Six single clones were isolated, expanded and harvested for gene analysis. One of the clones contained both E7 and TK genes as demonstrated by semi-quantitative PCR (lane 5, FIG. 6A), which suggested that a portion of MSCs were capable of fusing with tumor cells and achieving genetic material exchange, while other clones exhibited the presence of tk gene only (lanes 2, 3 and 6, FIG. 6A).

Discussions

Several mechanisms have been proposed to explain the host's inability to develop effective endogenous immunity against cancer, including generation of tumor variants lacking certain timorous antigens, loss of MHC expression, down-regulation of the antigen processing mechanism and also expression of inhibitory molecules which may promote the escape from immune surveillance including TGFβ and Fas ligand. A further significant contributor to the escape from immune surveillance is the induction of tolerance of mature T cells.

The dual components in the invention were designed to address two major problems mentioned above: the lack of tumor antigens and antigen-presenting ability. A cancer vaccine according to one embodiment of the invention comprises the following two components. The first component is an HPV 16 E6/E7-immortalized human mesenchymal stem cell line called KP-hMSCs. The insertion of HPV 16 E6/E7 genes served two functions. Firstly, the human mesenchymal stem cells were immortalized so that they could proliferate indefinitely and variations between different batches of primary stem cells could also be avoided. The immortalized KP-hMSCs have been thoroughly characterized and shown to be non-tumorigenic. Secondly, upon the infiltration, KP-hMSCs delivered the E6/E7 antigens into non-E6/E7 expressing tumor cells and thereby provided them with a potent tumor-associated antigen (TAA) and expanded the therapeutic spectrum of the E7 antigen-based protein vaccine.

The above conclusions are supported by the discoveries disclosed in the present application. Firstly, E7-mRNA transcript was detected in the tumor biopsies collected. Secondly, tumor-bearing mice co-treated with E7-expressing KP-hMSCs and E7-fusion protein vaccine exhibited the highest degree of inhibition in tumor growth and metastasis as monitored by planar γ-imaging. Thirdly, lung tissues collected from tumor-bearing mice treated with only KP-hMSCs or with only PE(ΔIII)-E7-KDEL3 fusion protein vaccine showed similar numbers of tumor nodules to those from untreated control mice (i.e., treated with PBS). Collectively, these findings indicated that KP-hMSCs served as an antigen-delivery system by successfully infiltrating into tumor cells and exposed and/or enhanced the exposure of the tumor cells to the immune surveillance system in vivo.

The detection of E7 antigen (from KP-hMSCs) in the tumor provided evidence that human MSCs successfully survived in immunological competent mice. This attribute plays an important role in the present invention and provides additional support that human MSCs can be engrafted into different species. Recent reports suggest that MSCs are capable of suppressing immunological reactions by secreting various kinds of chemokines and nitric oxide. This immunosuppressing ability could play a major role in the initial survival of KP-hMSCs followed by the subsequent immunoediting ability of NG4TK4 tumor cells once KP-hMSCs were incorporated into the tumor microenvironment. This notion was supported by the detection of E7 antigen in the lung tissues obtained from tumor-bearing mice treated with only KP-hMSCs. E7 antigen was, however, not detectable in the lung tissues collected from tumor-bearing mice receiving the combined treatment with KP-MSCs and PE(ΔIII)-E7-KDEL3. It was possible that E7-expressing KP-MSCs within the tumor were recognized and eliminated by the E7-fusion protein vaccine-mediated immunological attacks.

The majority of known tumor-associated antigens (TAAs) are associated with and presented by MHC class I molecules and recognized by tumor antigen-specific $CD8^+$-T cells, while a small number of TAAs are associated with MHC class II molecules and recognized by $CD4^+$-T cells. In previous pulmonary lung tumor studies, the fusion protein vaccine PE(ΔIII)-E7-KDEL3 elicited its anti-tumor effect via all venues of immunological responses including both $CD4^+$-T, $CD8^+$-T, and natural killer cells. Liao et al., (2005) "Fusion protein vaccine by domains of bacterial exotoxin linked with a tumor antigen generates potent immunologic responses and antitumor effects" *Cancer Res* 65: 9089-9098, which is herein incorporated by reference in its entirety. However, MHC II (or $CD4^+$-T cells) appeared to be the predominant route utilized by the combination therapy with KP-MSCs and PE(ΔIII)-E7-KDEL3 to deliver tumor-inhibitory effects. The addition of KP-hMSCs might have contributed to the different immunological responses triggered by the fusion protein vaccine PE(ΔIII)-E7-KDEL3 as compared to the results from previous studies using PE(ΔIII)-E7-KDEL3 to vaccinate mice before inoculation with TC-1 tumor cells. The TC-1 is a tumorigenic cell line established by transformation of lung epithelial cells of C57BL/6 mice with HPV16 E6, E7 and ras oncogene. See U.S. Pat. No. 7,378,100, which is herein incorporated by reference in its entirety. Because MSCs are capable of suppressing the immune system, it is possible that immunological reactions mediated by $CD8^+$-T cells could be somehow down-regulated by the incorporation of KP-MSCs into the therapy. In addition, the extent and the amount of E7 antigen tagged to the NG4TL4-STK tumor cells via incorporation of E7-expressing KP-MSCs could be much less as compared with the endogenous E7-antigen presented by TC-1 tumor cells.

Figure 6B:
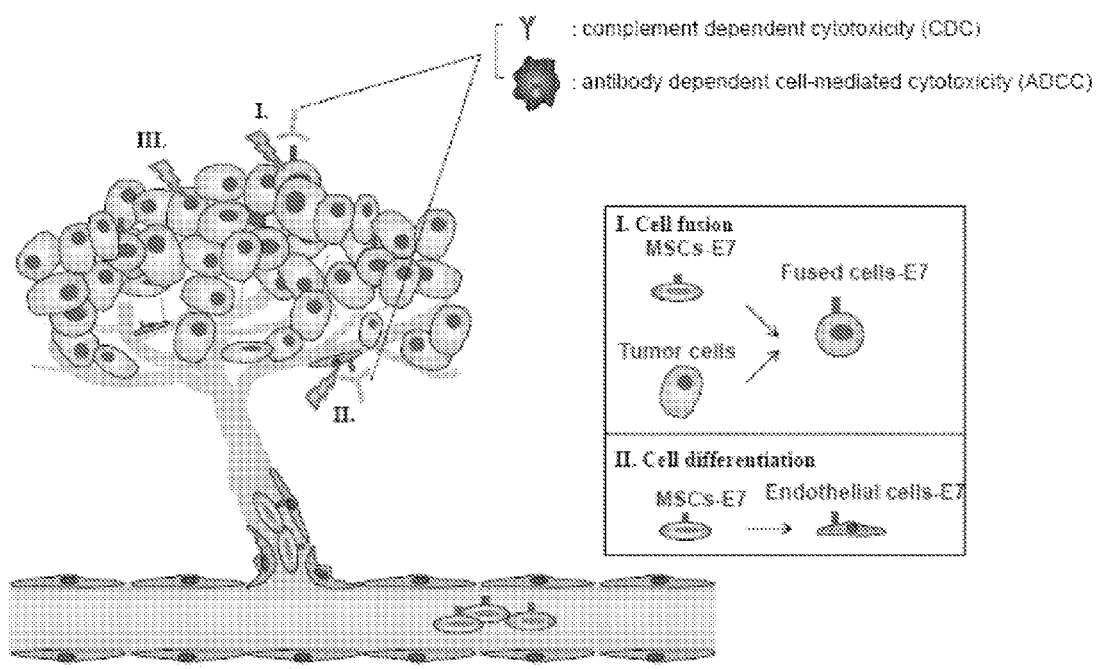
FIG. 6B is a schematic drawing showing two possible anti-tumor mechanisms underlying the combination treatment with the E7-fusion protein vaccine and KP-hMSCs.

The underlying molecular mechanisms responsible for the anti-cancer effects mediated by the combined treatment with KP-MSCs and PE(ΔIII)-E7-KDEL3 could be unique due to the involvement of MSCs. Based on the observation that KP-MSCs-infiltrated tumor cells were targeted and eliminated by anti-E7 antibody generated from the E7-fusion protein PE(ΔIII)-E7-KDEL3 inoculation, two possible scenarios were proposed. One scenario is that cell fusion occurred between the tumor cells and MSCs. MSCs have been shown to be fusogenic in nature. More importantly, the heterokaryon, i.e., fused progeny, contains genetic information from both parental cells. In vitro co-culture of E7-expressing, puromycin-resistant cord blood MSCs with neomycin-resistant NG4TL4-STK cells and selection of fusion progenies using both puromycin and neomycin lead to 6 clones. Among the six clones after dual antibiotic selections, one colony appeared to contain both E7 and tk genes, an indication of a successful cell fusion and incorporation of parental genetic information into the progeny (FIG. 6). The finding suggested that spontaneous fusion and genetic reprogramming between MSCs and tumor cells might be more frequent than they were previously considered. Cell fusion phenomenon could be one of the potential mechanisms for tumor inhibition induced by the combination treatment with KP-MSCs and PE(ΔIII)-E7-KDEL3.

Another scenario involves a possibility that the infiltrated KP-MSCs differentiated into tumor stromal cells. A previous study has demonstrated that the transplanted MSCs targeted to tumor and became part of the stroma. It was thus possible that the tumor stroma was tagged with E7-epitope as a result of MSCs incorporation. The circulating anti-E7 antibody generated from the E7-fusion protein vaccine recognized the antigen tagged on the tumor cells and then destroyed the tumor stroma, and thereby eliminated the tumor.

In summary, the invention relates to a novel anti-cancer therapy involving stem cells KP-MSCs and a fusion protein vaccine PE(ΔIII)-E7-KDEL3. The combined treatment appeared to effectively inhibit tumorigenesis and metastasis in the mouse tumor model. The discovery served as a platform for the future development of a universal treatment for different cancer types.

The amino acid sequence of wild-type E6 proteins is listed as SEQ ID NOs: 11 (NCBI Reference Sequence: NP_041325.1). For detoxified E6, there are two mutations at Cys70Gly and Cys113Gly.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for inhibiting growth and/or metastasis of a cancer cell, comprising:
   administering to a mammal in need thereof an effective amount of mesenchymal stem cells comprising a transgene encoding human papillomavirus (HPV) oncogenic protein selected from the group consisting of HPV E7, HPV E6 and a combination thereof, wherein the mesenchymal stem cells are immortal and show no signs of neoplastic transformation;
   administering to the mammal a vaccine composition comprising an effective amount of an immunogenic protein capable of eliciting an antibody specific against the HPV oncogenic protein selected from the group consisting of HPV E7, HPV E6 and a combination thereof;
   wherein the mesenchymal stem cells fuse with the cancer cell in the mammal, and wherein the fusion results in the expression of the HPV oncogneic protein selected from the group consisting of HPV E7, HPV E6 and a combination thereof on the cancer cell in the mammal; and
   wherein the antibody specific against the HPV oncogenic protein selected from the group consisting of HPV E7, HPV E6 and a combination thereof effects the death of the cancer cell expressing the HPV concogenic protein selected from the group consisting, of HPV E7, HPV E6 and a combination thereof in the mammal.

2. The method of claim 1, wherein the immunogenic protein comprises at least one Major Histocompatibility Complex (MHC) class II epitope.

3. The method of claim 1, wherein the elicited antibody triggers complement-dependent tumor cell lysis.

4. The method of claim 1, wherein the stem cells and the vaccine composition are sequentially administered to the mammal.

5. The method of claim 1, wherein the stem cells and the vaccine composition are concurrently administered, to the mammal.

6. The method of claim 1, wherein the mesenchymal stem cells are derived from bone marrow or cord blood.

7. The method of claim 1, wherein the cancer cell is at least one selected from the group consisting of a lung cancer cell and a sarcoma.

8. The method of claim 1, wherein the mammal has metastatic cancer.

9. The method of claim 1, wherein the immunogenic protein comprises it fusion protein comprising:
   (a) a *Psendomonas* exotoxin A (PE) fragment comprising a binding domain and a translocation domain and without a cytotoxic domain;
   (b) a human papillomavirus (HPV) Envelope protein selected from the group consisting of HPV E7, HPV E6, and a combination thereof; and
   (c) a carboxyl terminal moiety comprising an endoplasmic retention sequence.

* * * * *

SEQUENCE LISTING

```
<160> NUMBER OF SEQ ID NOS: 11

<210> SEQ ID NO 1
<211> LENGTH: 98
<212> TYPE: PRT
<213> ORGANISM: Human papillomavirus type 16

<400> SEQUENCE: 1

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 2
<211> LENGTH: 18
<212> TYPE: PRT
<213> ORGANISM: Artificial Sequence
<220> FEATURE:
<223> OTHER INFORMATION: Carboxyl terminal moiety Endoplasmic Reticulum
      Retention sequence

<400> SEQUENCE: 2

Lys Leu Asp Tyr Leu Lys Lys Asp Glu Leu Arg Asp Glu Leu Lys Asp
1               5                   10                  15

Glu Leu

<210> SEQ ID NO 3
<211> LENGTH: 9
<212> TYPE: PRT
<213> ORGANISM: Human adenovirus type 16

<400> SEQUENCE: 3

Arg Ala His Tyr Asn Ile Val Thr Phe
1               5

<210> SEQ ID NO 4
<211> LENGTH: 38
<212> TYPE: PRT
<213> ORGANISM: Human adenovirus type 16

<400> SEQUENCE: 4

Asp Ser Ser Glu Glu Glu Asp Glu Ile Asp Gly Pro Ala Gly Gln Ala
1               5                   10                  15

Glu Pro Asp Arg Ala His Tyr Asn Ile Val Thr Phe Cys Cys Lys Cys
            20                  25                  30
```

Asp Ser Thr Leu Arg Leu
            35

<210> SEQ ID NO 5
<211> LENGTH: 23
<212> TYPE: DNA
<213> ORGANISM: Artificial Sequence
<220> FEATURE:
<223> OTHER INFORMATION: HSV1-tk forward primer

<400> SEQUENCE: 5
tgcagcgacc cgcttaacag cgt                                             23

<210> SEQ ID NO 6
<211> LENGTH: 29
<212> TYPE: DNA
<213> ORGANISM: Artificial Sequence
<220> FEATURE:
<223> OTHER INFORMATION: HSV1-tk Reverse Primer

<400> SEQUENCE: 6
catagatctg gatccttccg gtattgtct                                       29

<210> SEQ ID NO 7
<211> LENGTH: 25
<212> TYPE: DNA
<213> ORGANISM: Artificial Sequence
<220> FEATURE:
<223> OTHER INFORMATION: HPV16 E6/E7 forward primer

<400> SEQUENCE: 7
atgcatagta tatagagatg ggaat                                           25

<210> SEQ ID NO 8
<211> LENGTH: 22
<212> TYPE: DNA
<213> ORGANISM: Artificial Sequence
<220> FEATURE:
<223> OTHER INFORMATION: HPV16 E6/E7 Reverse Primer

<400> SEQUENCE: 8
ctgcagcatc agccatggta ga                                              22

<210> SEQ ID NO 9
<211> LENGTH: 24
<212> TYPE: DNA
<213> ORGANISM: Artificial Sequence
<220> FEATURE:
<223> OTHER INFORMATION: GAPDH forward primer

<400> SEQUENCE: 9
gctctccaga acatcatccc tgcc                                            24

<210> SEQ ID NO 10
<211> LENGTH: 25
<212> TYPE: DNA
<213> ORGANISM: Artificial Sequence
<220> FEATURE:
<223> OTHER INFORMATION: GAPDH Reverse Primer

<400> SEQUENCE: 10
cgttgtcata ccaggaaatg agctt                                           25

<210> SEQ ID NO 11
<211> LENGTH: 158
<212> TYPE: PRT

```
<213> ORGANISM: Human papillomavirus type 16

<400> SEQUENCE: 11

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155
```